(12) United States Patent
Gorna et al.

(10) Patent No.: US 9,512,277 B2
(45) Date of Patent: Dec. 6, 2016

(54) AQUEOUS COMPOSITIONS AND METHODS FOR BONE HEMOSTASIS

(71) Applicants: Baxter International Inc., Deerfield, IL (US); Baxter Healthcare S.A., Glattpark (Opfikon) (CH)

(72) Inventors: Katarzyna I. Gorna, Vienna (AT); Andreas Goessl, Vienna (AT); Heinz Gulle, Gross-Enzersdorf (AT)

(73) Assignees: Baxter International, Inc., Deerfield, IL (US); Baxter Healthcare, S.A., Glattpark (Opfikon) (CH)

( * ) Notice: Subject to any disclaimer, the term of this patent is extended or adjusted under 35 U.S.C. 154(b) by 627 days.

(21) Appl. No.: 13/663,098

(22) Filed: Oct. 29, 2012

(65) Prior Publication Data

US 2013/0177601 A1    Jul. 11, 2013

Related U.S. Application Data

(60) Provisional application No. 61/553,032, filed on Oct. 28, 2011.

(51) Int. Cl.
| | |
|---|---|
| *C08G 81/00* | (2006.01) |
| *A61K 31/76* | (2006.01) |
| *A61L 24/04* | (2006.01) |
| *A61B 17/56* | (2006.01) |
| *A61K 31/765* | (2006.01) |
| *A61B 17/00* | (2006.01) |

(52) U.S. Cl.
CPC ............ *C08G 81/00* (2013.01); *A61K 31/765* (2013.01); *A61L 24/043* (2013.01); *A61L 24/046* (2013.01); *A61B 17/56* (2013.01); *A61B 2017/00933* (2013.01); *A61L 2400/04* (2013.01); *A61L 2430/02* (2013.01)

(58) Field of Classification Search
CPC ....... C08L 71/02; C08L 53/00; A61K 45/06; A61K 47/10; A61K 31/765; A61L 24/046; A61L 24/043; A61L 2400/04; A61L 2430/02; A61B 17/56; A61B 2017/00933
See application file for complete search history.

(56) References Cited

U.S. PATENT DOCUMENTS

| | | | |
|---|---|---|---|
| 6,194,515 B1 * | 2/2001 | Shinohara | C08L 59/00 428/35.2 |
| RE38,558 E | 7/2004 | Emanuele et al. | |
| 7,303,814 B2 * | 12/2007 | Lamberti et al. | 428/357 |
| 7,553,913 B2 | 6/2009 | Wellisz et al. | |
| 7,829,616 B2 | 11/2010 | Wellisz et al. | |
| 2003/0095945 A1 | 5/2003 | Levy et al. | |
| 2004/0245662 A1 | 12/2004 | Chaubal et al. | |
| 2006/0140904 A1 | 6/2006 | Wellisz et al. | |
| 2008/0317812 A1 | 12/2008 | Zhang et al. | |
| 2009/0117070 A1 | 5/2009 | Daniloff et al. | |
| 2009/0149954 A1 * | 6/2009 | Hu et al. | 623/16.11 |
| 2009/0270527 A1 * | 10/2009 | Lin et al. | 523/116 |
| 2009/0286886 A1 | 11/2009 | Fisher et al. | |
| 2010/0233269 A1 * | 9/2010 | Gorna et al. | 424/489 |
| 2011/0021964 A1 | 1/2011 | Larsen et al. | |
| 2011/0059151 A1 | 3/2011 | Buckland et al. | |

FOREIGN PATENT DOCUMENTS

WO    2011-128655    10/2011

OTHER PUBLICATIONS

Poloxamer (http://en.wikipedia.org/wiki/Poloxamer_407 (downloaded on Oct. 15, 2013)).*
Wellisz, T., et al., "Infection Rates and Healing Using Bone Wax and a Soluble Polymer Material," *Clinical Orthopaedics and Related Research*, 2008, vol. 466, pp. 481-486.
Fernandez-Tarrio, et al., "Pluronic and Tetronic Copolymers with Polyglycolyzed Oils as Self-Emulsifying Drug Delivery Systems", *American Association of Pharmaceutical Scientists PharmSciTech*, vol. 9, No. 2, (2008): p. 472.

* cited by examiner

*Primary Examiner* — Michael G Hartley
*Assistant Examiner* — Leah Schlientz
(74) *Attorney, Agent, or Firm* — Kilpatrick Townsend & Stockton LLP

(57) ABSTRACT

Bone hemostat compositions, and methods for their use and manufacture are provided. Exemplary hemostatic compositions include polymeric components such as random and non-random copolymers, natural polymers, ceramics, reactive group polymers, and combinations thereof. Bone compositions may be used during surgical procedures, and may be applied to bone to inhibit or prevent bleeding from bone.

25 Claims, 4 Drawing Sheets

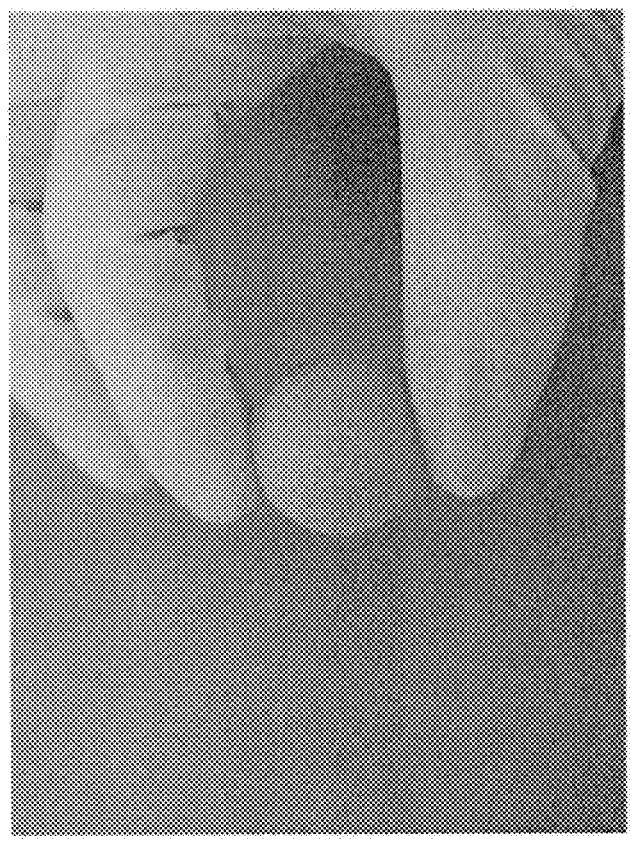
Fig 1. Aqueous bone hemostat with composition 4 given in Table 1

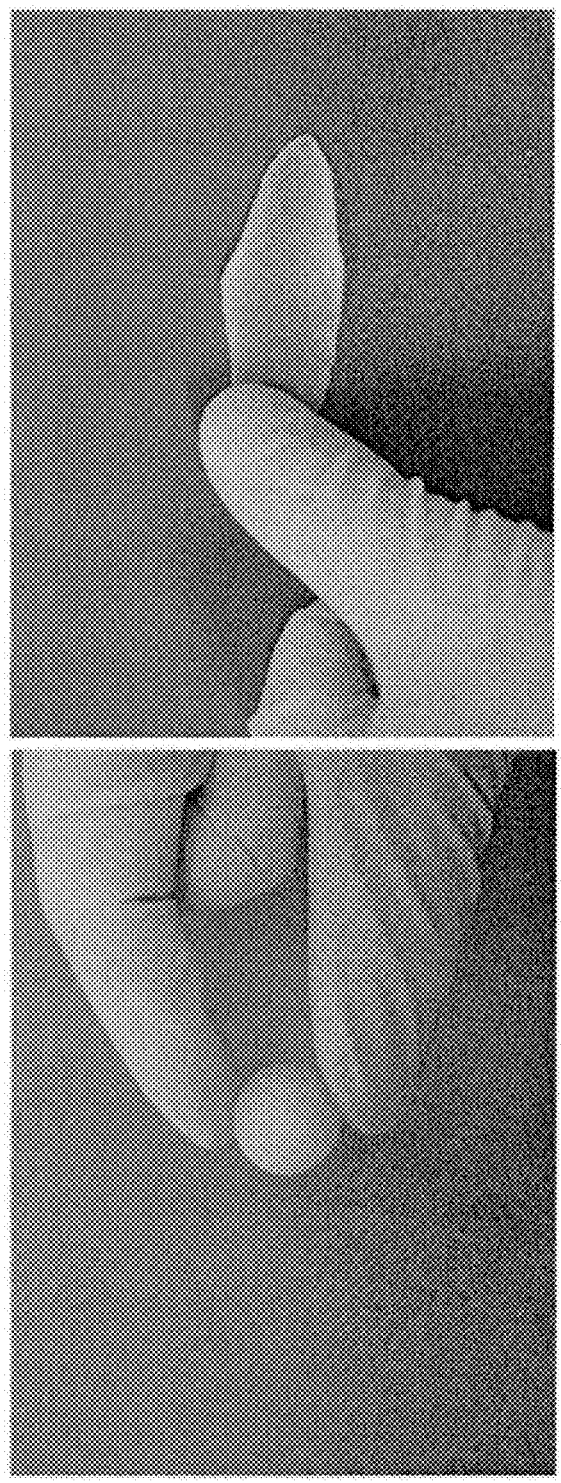
Fig 2. Non-aqueous bone hemostat with composition 2 given in Table 2

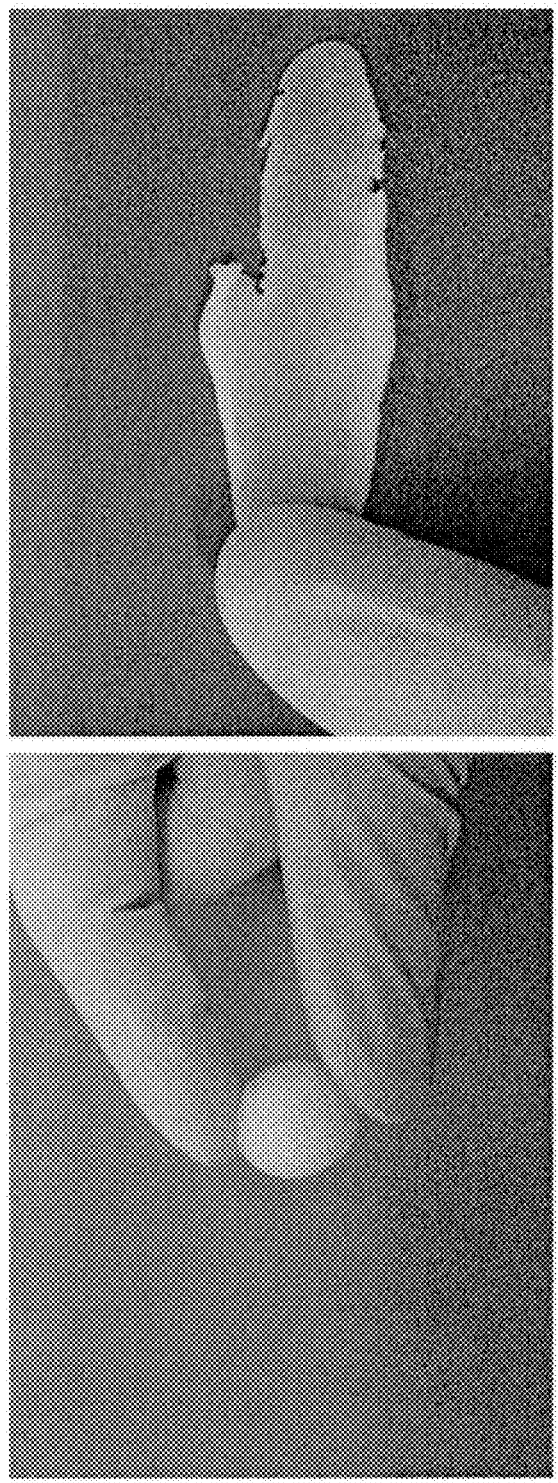
Fig 3. Non-aqueous bone hemostat with composition 5 given in Table 2

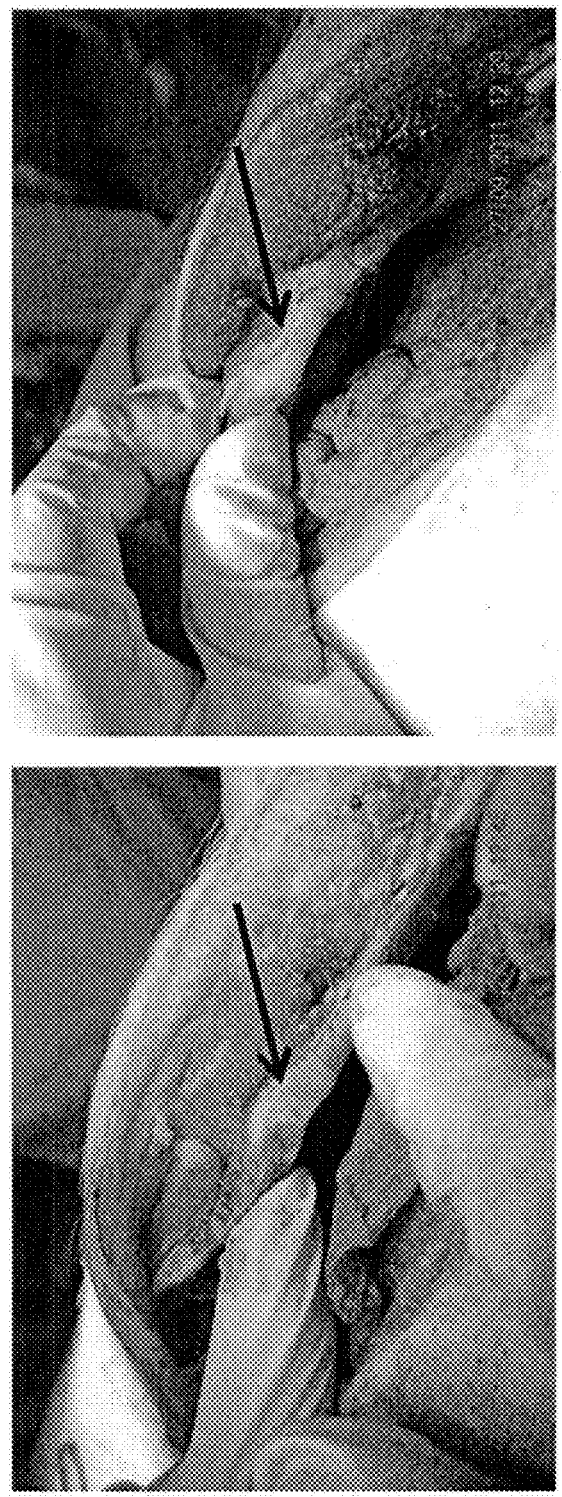
Fig 4. Examples of non-aqueous bone hemostats in sternotomy in heparinized pig.

AQUEOUS COMPOSITIONS AND METHODS FOR BONE HEMOSTASIS

RELATED APPLICATIONS

This application claims the benefit of U.S. Provisional Patent Application No. 61/553,032 filed Oct. 28, 2011, the content of which is incorporated herein by reference.

BACKGROUND OF THE INVENTION

Embodiments of the present invention relate generally to biocompatible materials, and more particularly to compositions for use in biomedical applications and methods of their manufacture.

Bones are living vascular organs which form part of the body's skeleton. Bones may include a variety of tissue types, including marrow, endosteum, periosteum, blood vessels, epithelium, nerves, cartilage, and mineralized osseous tissue. Bleeding from cut or disrupted bone is a common occurrence in many operative procedures. Excessive bleeding from bone during surgery may impair the surgeon's view of the operative field, may result in the need for blood transfusions, and may be associated with post-operative complications.

Cauterization techniques are used to control bleeding in soft tissue, but are ineffective for controlling bleeding in bone. Hence, bleeding in bone has traditionally been treated by using bone wax, a beeswax-based product that can be smeared across the cut surface to plug the holes in the bone, so as to reduce or stop the bleeding. More recently, synthetic bone hemostasis materials have been proposed, including Ostene (Ceremed Inc.) and HemaSorb (Orthocon Inc.).

Although bone hemostasis materials are currently available and provide real benefits to patients in need thereof, many advances may still be made to provide improved compositions for bone hemostasis. Embodiments of the present invention provide solutions to at least some of these outstanding needs.

BRIEF SUMMARY OF THE INVENTION

It is an object to provide a biocompatible material for use in biomedical applications which overcomes at least some of the problems or limitations associated with currently available bone hemostat products. Another object is to provide a biocompatible material which is a commercially acceptable alternative to currently available bone hemostat products.

Embodiments of the present invention encompass bone hemostat compositions, and methods for their use and manufacture. Bone hemostat compositions as disclosed herein can be administered to cut or damaged bone of a patient, for controlling, inhibiting, or preventing bleeding from the bone. Exemplary compositions for use in bone hemostasis include synthetic, resorbable, or soluble (e.g. water soluble) polymers that after application to a bleeding bone surface or site will remain in place temporarily to provide the desired effect of controlling blood flow, and will then disappear or disperse away from the treatment area within a few days, thus leaving space for new bone to grow. In some instances, a bone hemostat composition may be provided in a paste or paste-like form. In some instances, a bone hemostat composition may be provided in a doughy or dough-like form. According to some embodiments, a bone hemostat composition may be provided in a nonaqueous form that is a very viscous paste and dough-like.

Exemplary bone hemostat compositions may include granules, flakes, powders, or various combinations thereof, of any hemostatic and biodegradable components, and may be provided as molding compounds for bone or bone tissue. Exemplary bone hemostat compositions may optionally include natural polymer components, such as cross-linked gelatin particles, chitosan particles, or collagen particles, alone or in combination with ceramic particles such as particles of hydroxyapatite, Si-hydroxyapatite or Sr substituted biphasic ceramic, in a moldable, malleable carrier based on polymer compositions or blends.

Various formulations based on non-random and random copolymer compositions, including without limitation Poloxamer 407, Pluronics with hydrophobic properties (e.g. L-31, L61), and Pluriol V-10, along with other polymer components such as polyethylene glycol of various molecular weights, can be used in the preparation of polymer compositions or blends for a bone hemostat or bone hemostat with enhanced hemostatic and osteogenic properties. Bone hemostat compositions with enhanced hemostatic properties may also include natural polymer components such as gelatin and cross-linked derivatives thereof, chitosan, or collagen, such as, for example, cross-linked gelatin particles, chitosan particles, or collagen particles, as a filler. In some embodiments, inorganic particles based on nanosize hydroxyapatite, siliconated hydroxyapatite biphasic ceramic, Sr substituted biphasic ceramic, and the like, are used as an osteogenic filler for bone hemostat.

Exemplary bone hemostat compositions may be provided as a malleable paste. For example, embodiments encompass a malleable, ready-to use hemostat for application in bone.

Exemplary bone hemostat compositions may include a synthetic polymeric matrix, optionally combined with hemostatic agents, antibiotics, or ceramic particles or powders. Bone hemostat paste compositions disclosed herein may be provide in a ready-to-use form for bone hemostasis, that does not require any preparation such as pre-warming or kneading. Exemplary bone hemostat compositions exhibit a reasonably short dissolution time. Exemplary bone hemostat compositions disclosed herein can be formulated so as not to change their handling characteristics upon kneading or application to a bone site, which may be bleeding, damaged, or otherwise compromised.

Embodiments of the present invention encompass bone hemostat compositions that stop or inhibit bone bleeding upon application, resist irrigation, and remain in place for a duration sufficient to achieve stable hemostasis. Exemplary bone hemostat compositions are formulated to offer controlled, precise application, and to conform to the site of care. In some embodiments, bone hemostat compositions may be ready for use directly out of the package, and do not require warming or kneading prior to application to the patient's bone. In some instances, bone hemostat compositions as disclosed herein are absorbed in the patient's body within 30 days. Exemplary bone hemostat compositions can permit normal bone healing and promote bone regeneration. In some instances, bone hemostat compositions can reduce hematoma formation. What is more, exemplary bone hemostats can be used as carriers for medications including anti-inflammatory drugs which may be used to reduce inflammation at the surgery site. Embodiments of the present invention provide polymeric formulations with superior handling properties for bone hemostasis.

In one aspect, embodiments of the present invention encompass biocompatible compositions for use as a bone hemostat. Exemplary compositions include any of the compositions disclosed herein. For example, a bone hemostat composition may include a polyoxyethylene-polyoxypropylene block copolymer. In some cases, such a block copolymer may have a molecular weight (Mw) within a range from about 9800 Mw to about 16300 Mw. Embodiments of the present invention also encompass methods of treating an individual or patient, which may include administering a biocompatible composition as disclosed herein to a bone of the patient, for example for the purpose of inhibiting or controlling bleeding from the bone. What is more, embodiments of the present invention encompass kits for the treatment of a bone of an individual or patient. In some instances, kits may include a biocompatible composition as disclosed herein, and instructions for use.

In another aspect, embodiments of the present invention encompass compositions for use as a bone hemostat, and methods of their manufacture. In some instances, biocompatible bone hemostat compositions may be provided as an aqueous solution. In some instances, biocompatible bone hemostat compositions may be provided as a nonaqueous solution. Exemplary biocompatible bone hemostat compositions may include water, such that the composition is hydrated or present as an aqueous composition. In some cases, compositions include a polyoxyethylene-polyoxypropylene block copolymer having a molecular weight (Mw) within a range from about 9800 Mw to about 16300 Mw. In some instances, the polyoxyethylene-polyoxypropylene block copolymer is a triblock copolymer. In some instances, the polyoxyethylene-polyoxypropylene block copolymer has a molecular weight (Mw) within a range from about 9800 Mw to about 14600 Mw. In some cases, the block copolymer has a percentage of polyethylene oxide within a range from about 60% to about 80%. In some cases, the block copolymer has a percentage of polypropylene oxide within a range from about 20% to about 40%. In some cases, the polyoxyethylene-polyoxypropylene block copolymer has 202 ethylene oxide units and 56 propylene oxide units. In some cases, the composition includes water and is hydrated. In some cases, water is present in the composition within a range from about 20% to about 45% by weight of the composition, and a polyoxyethylene-polyoxypropylene block copolymer is present in the composition within a range from about 20% to about 80% by weight of the composition. According to some embodiments, compositions may include natural polymers such as gelatin, chitosan, or collagen. For example, compositions may include natural polymer particles such as gelatin particles, chitosan particles, or collagen particles. In some cases, a biocompatible composition may include water and cross linked gelatin particles, where the water is present at about 44.4% by weight of the composition, a polyoxyethylene-polyoxypropylene block copolymer is present at about 33.3% weight of the composition, and the cross linked gelatin particles are present at about 22.2% weight of the composition. In some cases, a biocompatible composition may include water and cross linked gelatin particles, where the water is present within a range from about 20% to about 50% by weight of the composition, a polyoxyethylene-polyoxypropylene block copolymer is present within a range from about 20% to about 40% weight of the composition, and the cross linked gelatin particles are present within a range from about 20% to about 40% weight of the composition. In some cases, a biocompatible composition may include an ethylene glycol polymer and an oxazoline polymer. For example, the oxazoline polymer may be present within range from about 2% to about 10% by weight of the composition. In some instances, a biocompatible composition may include water, an ethylene glycol polymer, an oxazoline polymer, and cross linked gelatin particles or other natural polymer particles. For example, the water can be present at about 24.4% by weight of the composition, the polyoxyethylene-polyoxypropylene block copolymer can be present at about 26.7% weight of the composition, the ethylene glycol polymer can be present at about 13.3% by weight of the composition, the oxazoline polymer can be present at about 2.7% by weight of the composition, and the cross linked gelatin particles can be present at about 33.3% weight of the composition. In some cases, a biocompatible composition may include an ethylene glycol polymer, a random alkylene oxide copolymer, and an oxazoline polymer. In some cases, a biocompatible composition may include water, an ethylene glycol polymer, a random alkylene oxide copolymer, an oxazoline polymer, and cross linked gelatin particles or other natural polymer particles such as chitosan or collagen particles. For example, water can be present at about 27% by weight of the composition, a polyoxyethylene-polyoxypropylene block copolymer can be present at about 20% weight of the composition, the ethylene glycol polymer can be present at about 10% by weight of the composition, the random alkylene oxide copolymer can be present at about 5% by weight of the composition, the oxazoline polymer can be present at about 3% by weight of the composition, and the cross linked gelatin or other natural polymer particles can be present at about 35% weight of the composition. In some cases, a biocompatible composition may include an ethylene glycol polymer, a random alkylene oxide copolymer, an oxazoline polymer, and ceramic particles. In some instances, a biocompatible composition may include water, an ethylene glycol polymer, a random alkylene oxide copolymer, an oxazoline polymer, cross linked gelatin or other natural polymer particles, and ceramic particles. For example, water can be present at about 27% by weight of the composition, the polyoxyethylene-polyoxypropylene block copolymer can be present at about 20% weight of the composition, the ethylene glycol polymer can be present at about 10% by weight of the composition, the random alkylene oxide copolymer can be present at about 5% by weight of the composition, the oxazoline polymer can be present at about 3% by weight of the composition, the cross linked gelatin particles or other natural polymer components can be present at about 30% weight of the composition, and the ceramic particles can be present at about 5% weight of the composition. In some instances, ceramic particles may include Si-substituted hydroxyapatite particles. In some instances, ceramic particles may include Sr-substituted hydroxyapatite particles or Sr-substituted biphasic ceramic particles. In some instances, the ceramic particles include Si-substituted hydroxyapatite particles having particle size less than about 150 μm. In some instances, a random alkylene oxide copolymer of the composition has an ethylene oxide to propylene oxide ratio of about 1:1.

In yet another aspect, embodiments of the present invention encompass compositions for use as a bone hemostat, and methods of their manufacture. Exemplary biocompatible bone hemostat compositions may contain little or no water, and thus may be present as an anhydrous composition, an unhydrated composition, or a nonaqueous composition. In some cases, compositions include a polyoxyethylene-polyoxypropylene block copolymer having a molecular weight (Mw) within a range from about 9800 Mw to about 16300 Mw. In some instances, the polyoxyethylene-polyoxypropylene block copolymer is a triblock copolymer. In some instances, the polyoxyethylene-polyoxypropylene block copolymer has a molecular weight (Mw) within a range from about 9800 Mw to about 14600 Mw. In some cases, the block copolymer has a percentage of polyethylene oxide within a range from about 60% to about 80%. In some cases, the block copolymer has a percentage of polypropylene oxide within a range from about 20% to about 40%. In some cases, the polyoxyethylene-polyoxypropylene block copolymer has 202 ethylene oxide units and 56 propylene oxide units. In some instances, compositions may include a random alkylene oxide copolymer. For example, compositions may include a polyoxyethylene-polyoxypropylene block copolymer that is present at about 57.1% weight of the composition, and a random alkylene oxide copolymer that is present at about 42.9% by weight of the composition. In some cases, a biocompatible composition includes a random alkylene oxide copolymer, where a polyoxyethylene-polyoxypropylene block copolymer is present within a range from about 45% to about 80% by weight of the composition, and the random alkylene oxide copolymer is present within a range from about 20% to about 55% by weight of the composition. In some cases, a biocompatible composition includes a random alkylene oxide copolymer and ceramic particles. For example, a biocompatible composition may include a polyoxyethylene-polyoxypropylene block copolymer that is present at about 44.4% weight of the composition, a random alkylene oxide copolymer that is present at about 44.4% by weight of the composition, and ceramic particles that are present at about 11.2% weight of the composition. In some cases, a biocompatible composition may include a polyoxyethylene-polyoxypropylene block copolymer that is present within a range from about 40% to about 80% by weight of the composition, a random alkylene oxide copolymer that is present within a range from about 20% to about 50% by weight of the composition, and ceramic particles that are present within a range from about 5% to about 20% by weight of the composition. In some instances, a biocompatible composition may include a random alkylene oxide copolymer and a second polyoxyethylene-polyoxypropylene block copolymer. For example, a biocompatible composition may include a polyoxyethylene-polyoxypropylene block copolymer that is present at about 50% weight of the composition, a random alkylene oxide copolymer that is present at about 25% by weight of the composition, and a second polyoxyethylene-polyoxypropylene block copolymer that is present at about 25% weight of the composition. Relatedly, a biocompatible composition may include a polyoxyethylene-polyoxypropylene block copolymer that is present within a range from about 40% to about 70% by weight of the composition, a random alkylene oxide copolymer that is present within a range from about 5% to about 40% by weight of the composition, and a second polyoxyethylene-polyoxypropylene block copolymer that is present within a range from about 5% to about 30% by weight of the composition. In some instances, a second polyoxyethylene-polyoxypropylene block copolymer may include 4 ethylene oxide units and 16 propylene oxide units. In some cases, a biocompatible composition may include a random alkylene oxide copolymer, a second polyoxyethylene-polyoxypropylene block copolymer, and ceramic particles. For example, a biocompatible composition may include a polyoxyethylene-polyoxypropylene block copolymer that is present at about 44.4% weight of the composition, a random alkylene oxide copolymer that is present at about 22.2% by weight of the composition, a second polyoxyethylene-polyoxypropylene block copolymer that is present at about 22.2% weight of the composition, and ceramic particles that are present at about 11.2% weight of the composition. In some instances, a biocompatible composition may include a polyoxyethylene-polyoxypropylene block copolymer that is present at about 57.1% weight of the composition, a random alkylene oxide copolymer that is present at about 14.3% by weight of the composition, and a second polyoxyethylene-polyoxypropylene block copolymer that is present at about 28.6% weight of the composition. A second polyoxyethylene-polyoxypropylene block copolymer may include 4 ethylene oxide units and 32 propylene oxide units. In some cases, a biocompatible composition may include a polyoxyethylene-polyoxypropylene block copolymer that is present at about 50% weight of the composition, a random alkylene oxide copolymer that is present at about 25% by weight of the composition, and a second polyoxyethylene-polyoxypropylene block copolymer that is present at about 25% weight of the composition. A second polyoxyethylene-polyoxypropylene block copolymer may include 4 ethylene oxide units and 32 propylene oxide units. In some cases, a biocompatible composition may include a random alkylene oxide copolymer, a second polyoxyethylene-polyoxypropylene block copolymer, and ceramic particles. For example, a biocompatible composition may include a polyoxyethylene-polyoxypropylene block copolymer that is present at about 50.7% weight of the composition, a random alkylene oxide copolymer that is present at about 12.7% by weight of the composition, a second polyoxyethylene-polyoxypropylene block copolymer that is present at about 25.4% weight of the composition, and ceramic particles that are present at about 11.2% weight of the composition. In some instances, ceramic particles may include Si-substituted hydroxyapatite particles. In some instances, ceramic particles may include Si-substituted hydroxyapatite particles having particle size less than about 150 µm. In some instances, ceramic particles may include Sr-substituted biphasic ceramic particles.

In another aspect, embodiments of the present invention encompass methods of treating a patient, which include administering a biocompatible composition as disclosed herein to a bone of the patient. Relatedly, embodiments of the present invention encompass kits for the treatment of a bone of a patient. Exemplary kits may include a biocompatible composition as disclosed herein, and instructions for using the composition to treat a bone of a patient.

In another aspect, embodiments of the present invention encompass methods of manufacturing an aqueous or hydrated biocompatible composition as disclosed herein. For example, methods may include combining water with one or more polymers, which may include a polyoxyethylene-polyoxypropylene block copolymer having a molecular weight (Mw) within a range from about 9800 Mw to about 16300 Mw, to obtain a homogeneous paste. Methods may also include combining natural polymer components, such as gelatin, chitosan, or collagen with the paste. Relatedly, methods may also include combining ceramic particles with the paste. The components can be further mixed to obtain a homogeneous product.

In yet another aspect, embodiments of the present invention encompass methods of manufacturing a nonaqueous biocompatible composition as disclosed herein. For example, methods may include combining one or more polymers, which may include a polyoxyethylene-polyoxypropylene block copolymer having a molecular weight (Mw) within a range from about 9800 Mw to about 16300 Mw, optionally with ceramic and/or natural polymer particles, to obtain a homogenous material. Further, methods may include heating the combined material above a melting point, or otherwise bringing the composition to a molten state. Methods may also include allowing air bubbles to escape from the melted material, and allowing the melted material to solidify. Additional mixing and homogenization of the material can be performed.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

BRIEF DESCRIPTION OF THE DRAWINGS

Illustrative embodiments of the present invention are described in detail below with reference to the following drawing figures:

FIG. 1 shows an aqueous bone hemostat composition according to embodiments of the present invention.

FIG. 2 shows a non-aqueous bone hemostat composition according to embodiments of the present invention.

FIG. 3 shows a non-aqueous bone hemostat composition according to embodiments of the present invention.

FIG. 4 depicts use of non-aqueous bone hemostat compositions according to embodiments of the present invention.

DETAILED DESCRIPTION OF THE INVENTION

Embodiments of the present invention encompass biocompatible compositions for use in bone hemostasis. In some cases, bone hemostat compositions may include polyoxyethylene-polyoxypropylene block copolymers, natural polymers, ceramic particles, ethylene glycol polymers, oxazoline polymers, and various combinations or blends thereof. Optionally, bone hemostat compositions may be formulated as aqueous compositions or as nonaqueous compositions.

Definitions of a number of terms used throughout the specification are provided below.

The term "biocompatible material" used herein encompasses a material that does not threaten, impede, or adversely affect living tissue.

The term "resorbable polymer matrix" used herein encompasses a polymer composition which can be gradually dissolved and eliminated from the body.

The term "copolymer" used herein (also known as a heteropolymer) encompasses a polymer derived from two or more types of monomeric species. This is in contrast to a homopolymer where only one type of monomer is used.

The term "non-random" used herein encompasses an intra-chain distribution of co-monomers having a particular pattern that is segmented. It is a unique structural feature of a block copolymer.

The term "poloxamer" used herein encompasses a nonionic triblock copolymer composed of a central hydrophobic chain of polyoxypropylene(poly(propylene oxide)) flanked by two hydrophilic chains of polyoxyethylene(poly(ethylene oxide)). In some instances, a poloxamer may be referred to as a polyoxyethylene-polyoxypropylene (POE-POP) block copolymer.

The term "number average molecular weight" used herein is calculated as follows:

$$M_w = \frac{\Sigma_i N_i M_i^2}{\Sigma_i N_i M_i}$$

where $N_i$ is the number of molecules of molecular weight $M_i$.

The term "bone hemostasis" refers to a process of inhibiting, preventing, or otherwise modulating or controlling bleeding in bone. Relatedly, the terms "bone hemostat" encompasses compositions that can be applied or administered to bone, for the intended purpose of achieving or facilitating bone hemostasis.

Each aspect or embodiment described herein may be combined with any other aspect(s) or embodiment(s) unless clearly indicated to the contrary. In particular any feature indicated as being preferred or advantageous may be combined with any other feature or features indicated as being preferred or advantageous.

The biocompatible material described herein is suitable for use in therapy. Such therapy includes, but is not restricted to, medicine, dentistry and surgery. More specific applications include use of the polymer composition as a hemostatic agent or a carrier for medication.

In exemplary biocompatible materials, a resorbable polymer matrix can provide a continuous phase, and additives or particles can provide a non-continuous, dispersed phase.

Primary Non-Random Copolymer Components

Embodiments of the present invention encompass compositions having one or more primary non-random copolymer components. For example, bone hemostat compositions may include at least one non-random copolymer of poly (alkylene oxide)s or derivatives thereof. A non-random copolymer of poly(alkylene oxide)s can be linear or branched. Exemplary poly(alkylene oxide)s may include polyoxyethylene-polyoxypropylene (POE-POP) block copolymers or poloxamers, and may contain poly(ethylene oxide) (EO) and polypropylene oxide) (PO) units with the molecular formula $(EO)_x(PO)_y(EO)_x$. Often, a non-random copolymer will include at least two poly(alkylene oxide)s. In some embodiments, a non-random copolymer of poly(alkylene oxide)s has a number average molecular weight within a range from about 9,840 to about 14,600 g/mol. In some embodiments, a non-random copolymer of poly(alkylene oxide)s has a number average molecular weight within a range from about 6,500 to about 16,300 g/mol. Relatedly, in some cases, the molecular weight may be determined based on an end group analysis approach. The number average molecular weight of the poly(alkylene oxide) may be selected so as to confer certain handling properties, such as a desired deformation force or working window, to the bone hemostat composition. As further discussed elsewhere herein, a non-random copolymer, for example in conjunction with other components of the bone hemostat composition, can operate to facilitate blood wicking and clotting.

In some embodiments, the polyoxypropylene core of a poloxamer has an average molecular weight in the range from about 3200 to about 4100 g/mol. Relatedly, a poloxamer may have a polyoxypropylene core of 56 units (e.g. 3248 g/mol) or 70 units (e.g. 4060 g/mol). In some embodiments, a poloxamer has a polyoxyethylene content of from about 25% to about 30%. In some embodiments, the bone hemostat composition may include poloxamer 407 (Pluronic F127), which is a commercially available polyoxyethylene-polyoxypropylene triblock copolymer of the formula $(EO)_{101}(PO)_{56}(EO)_{101}$. In some embodiments, a bone hemostat composition may include a polyoxyethylene-polyoxypropylene triblock copolymer of the formula $(EO)_{106}(PO)_{70}(EO)_{106}$, or for example $(EO)_{106}(PO)_{69}(EO)_{106}$. Depending on the values of x and y in the formula $(EO)_x(PO)_y(EO)_x$, the molecular weight and/or the PO percentage of the poloxamer may vary. It has been observed that bone hemostat compositions containing poloxamer 407 have excellent handling properties.

Exemplary compositions may incorporate poloxamers that are present in solid form, as compared to, for example, a wax form. In some instances, a poloxamer may include a percentage of PO of between about 20% and about 40%. In some instances, the percentage of PO in a poloxamer may be about 30%. By adjusting the amount or percentage of PO block or polyoxypropylene core, it may be possible to control or modulate the solubility of the composition. For example, use of a poloxamer having a relatively higher PO concentration or amount may provide a bone hemostat composition that dissolves in the body at a relatively lower rate, as compared to that of a poloxamer having a lower PO concentration or amount. If, however, the amount of PO in the poloxamer is excessively high, the resulting bone hemostat composition may be highly hydrophobic, and may not dissolve quickly enough to provide a desired therapeutic or treatment effect. Other poloxamers which may be used include Pluronic F77/poloxamer 217 (30% PO), Pluronic F87/poloxamer 237 (30% PO), Pluronic F88/poloxamer 238 (20% PO), Pluronic F98/poloxamer 288 (20% PO), Pluronic F108/poloxamer 388(20% PO), and Pluronic F68/poloxamer188 (20% PO).

According to embodiments of the present invention, one or more primary non-random copolymer components may be used, optionally in combination with other components as described elsewhere herein, to prepare a matrix for a bone hemostat paste. The solubility of non-random copolymer components, optionally in combination with other components as described elsewhere herein, can be tailored to obtain a bone hemostat composition with desired dissolution kinetics, for example by blending polymers with different hydrophilic-hydrophobic properties or by blending soluble and poorly soluble polymers.

Secondary Non-Random Copolymer Components

Embodiments of the present invention encompass compositions having one or more secondary non-random copolymer components. For example, bone hemostat compositions may include at least one secondary non-random copolymer of poly(alkylene oxide)s or derivatives thereof, in addition to a primary non-random copolymer. Exemplary poly(alkylene oxide)s may include polyoxyethylene-polyoxypropylene (POE-POP) block copolymers or poloxamers, and may contain poly(ethylene oxide) (EO) and poly(propylene oxide) (PO) units with the molecular formula $(EO)_x(PO)_y(EO)_x$. Often, a non-random copolymer will include at least two poly(alkylene oxide)s. In some instances, a secondary non-random copolymer component may be more hydrophobic, or less water miscible, than a primary non-random copolymer component. The presence of such secondary non-random copolymer components in addition to a primary non-random copolymer can operate to reduce, slow down, or modulate dissolution of the bone hemostat composition.

In some embodiments, a non-random copolymer of poly(alkylene oxide)s has a weight average molecular weight within a range from about 1,100 to about 5,000 g/mol, and a percentage of polyoxypropylene from about 60% to about 90%, or higher. For example, an exemplary secondary non-random copolymer may include Pluronic L31, which is a commercially available polyoxyethylene-polyoxypropylene triblock copolymer of the formula $(EO)_2(PO)_{16}(EO)_2$. Another exemplary secondary non-random copolymer may include Pluronic L61, which is a commercially available polyoxyethylene-polyoxypropylene triblock copolymer of the formula $(EO)_3(PO)_{30}(EO)_3$. Pluronic L62 with the formula $(EO)_5(PO)_{30}(EO)_5$, Pluronic L63 with the formula $(EO)_9(PO)_{30}(EO)_9$, Pluronic L72 with the formula $(EO)_6(PO)_{35}(EO)_6$, Pluronic L81 with the formula $(EO)_3(PO)_{39}(EO)_3$, Pluronic L92 with the formula $(EO)_8(PO)_{47}(EO)_8$, Pluronic L101 with the formula $(EO)_4(PO)_{56}(EO)_4$, Pluronic L122 with the formula $(EO)_{11}(PO)_{69}(EO)_{11}$ are other block copolymers which may be used as a secondary non-random copolymer component.

According to embodiments of the present invention, one or more secondary non-random copolymer components may be used, optionally in combination with other components as described elsewhere herein, to prepare a matrix for a bone hemostat paste. The solubility of non-random copolymer components, optionally in combination with other components as described elsewhere herein, can be tailored to obtain a bone hemostat composition with desired dissolution kinetics, for example by blending polymers with different hydrophilic-hydrophobic properties or by blending soluble and poorly soluble polymers.

In some cases, a secondary non-random copolymer component may be provided as a liquid, or as a viscous liquid. In some cases, a secondary non-random copolymer component may be more hydrophobic that the primary non-random copolymer component.

Random Copolymer Components

Embodiments of the present invention encompass compositions having one or more random copolymer components. For example, bone hemostat compositions may include at least one random copolymer of poly(alkylene oxide)s or derivatives thereof. Exemplary poly(alkylene oxide)s may include polyoxyethylene-polyoxypropylene (POE-POP) copolymers, and may contain random arrangements of poly(ethylene oxide) (EO) and poly(propylene oxide) (PO) units.

Random copolymers of poly(alkylene oxide)s are commercially available from a variety of manufacturers including BASF, Dow Chemical, and Sigma/Aldrich under the trade names PLURADOT®, PLURACOL®, SYNALOX® EPB, and EMKAROX® among others. They are available in a range of EO:PO ratios and molecular weights (e.g., 1000 to 22,000 g/mol) and in linear and branched geometries, and are commonly characterized by their viscosity rather than molecular weight. Dow Chemical provides a number of random copolymers of poly(alkylene oxide)s with molecular weights in the range of 1,500 to 4,900 including those with the following codes: EP 530, EP 1730, EP 435, EP 1660, 15-200, 112-2, UCON 50-HB-5100, and UCON 50-HB-660. Sigma/Aldrich provides a number of random copolymers of poly(alkylene oxide)s with molecular weights in the range of 2,500 to 12,000 including those with the following codes: 43,819-7, 43,820-0, 43,818-9, 40,918-9.

According to some embodiments, an exemplary random copolymer component includes a random alkylene oxide copolymer having a weight average molecular weight of about 22,000 g/mol and an EO:PO mass ratio of about 50:50.

Such a compound is commercially available from BASF Corporation as PLURACOL® V-10 or PLURIOL® V-10. Often, a random copolymer will include at least two poly (alkylene oxide)s. In some cases, random copolymer components may operate to improve cohesiveness and moldability of a bone hemostat compositions. In some cases, bone hemostat compositions may be present as an aqueous paste that includes a random copolymer component within a range from about 2% to about 10% by weight of the composition.

Basic Matrix for Soluble Bone Hemostat

Embodiments of the present invention encompass the use of various polymeric compositions to provide a basic matrix for soluble bone hemostat composition. In some embodiments, one or more primary non-random copolymer components can be used to prepare such a basic matrix. Relatedly, a one or more primary non-random copolymer components, optionally in combination with one or more secondary non-random copolymer components, and/or one or more random copolymer components, can be mixed at various ratios to provide a basic matrix for soluble bone hemostat. For example, it is possible to prepare a basic matrix for soluble bone hemostat by mixing Pluronic F127, Pluronic L-61, Pluronic L-31, and Pluriol V10 at selected ratios, as discussed elsewhere herein.

A primary non-random copolymer component (e.g. Pluronic F127) may be a solid polymer that after melting will form a hard and brittle material. A secondary non-random copolymer component (e.g. Pluronic L-61 or Pluronic L-31) may be a liquid polymer that is hydrophobic. When blended, the combined primary and secondary non-random copolymer component may provide a material with soft, malleable properties. A random copolymer component (e.g. Pluriol V10) may be a very viscous polymer with hydrophobic properties, and when blended with a primary non-random copolymer component (e.g. Pluronic F127) may provide a resulting material with good handling properties. Some random copolymer components may high molecular weights, strong hydrophobic properties, and low miscibility in water. In some embodiments, compositions containing random copolymer components may also include secondary non-random copolymer components of low molecular weight (e.g. Pluronic L-31 or Pluronic L-61). Such secondary non-random copolymer components may operate as a kind of plasticizer for a primary non-random copolymer component (e.g. Pluronic F127), and in some situations may allow for a reduction in the amount of random copolymer component (e.g. Pluriol V10) in a bone hemostat composition. According to some embodiments, bone hemostat compositions containing certain combinations of primary and secondary non-random copolymer components and random copolymer components in ready-to-use paste with superior handling properties. The presence or ratios of such components can affect the handling properties of a bone hemostat composition. Similarly, the presence or ratios of such components can affect the dissolution kinetic of a bone hemostat composition.

The presence of hemostatic additives in poloxamer compositions can improve or provide blood wicking and clotting at the local defect site. Poloxamers may operate as a mechanical barrier, by obstructing the bleeding vessels. Polymeric compositions or blends can be used alone, or in some instances as a carrier or a matrix for antibiotics, blood coagulants or related materials including natural polymer components such as gelatin and cross-linked derivatives, for example cross-linked gelatin particles, or osteoconductive ceramics.

Natural Polymer Components

Exemplary bone hemostat polymeric blends or compositions can be also formulated with natural polymers such as gelatin or cross-linked derivatives thereof, for example cross-linked gelatin particles. Other natural polymer components may chitosan or collagen. Such natural polymers can be incorporated into bone hemostat compositions in the form of a fine powder, having small particles with a diameter of 500 µm or less, or as short fibers (0.2-2 mm), for example. The presence of such natural polymers may enhance hemostatic properties of the polymeric blends or compositions and may enhance process of bone healing or regeneration. Natural polymer components can be use as an additive, in combination with a soluble polymer matrix that includes a triblock copolymer, for example. In bone hemostat compositions containing gelatin, the relative amounts of water, block copolymer, and gelatin may be adjusted or selected based on the ratio of solid to liquid components in the composition. For example, where more water is used, it is possible to use more gelatin. Relatedly, where more poloxamer is used, it is possible to use less gelatin. In bone hemostat compositions containing chitosan or collagen, the chitosan or collagen can be similarly adjusted or selected. According to some embodiments, natural polymers for use with bone hemostat compositions may include cross-linked or non-cross-linked chitin, chitosan, gelatin, collagen, as well as cross-linked or non-cross-linked derivatives thereof. Table 1, discussed elsewhere herein, provides exemplary composition formulations containing cross-linked gelatin particles. Any wt % amounts or ranges mentioned with reference to gelatin can also apply to other natural polymers such as the chitin, chitosan, and collagen variants disclosed herein.

Ceramic Particle Components

Similarly, the presence of ceramic particles can have positive impact on bone regeneration and can also stimulate hemostasis by release of calcium ions from ceramic materials. Any type of ceramic may be used. For example, ceramic particles can be calcium carbonate, hydroxyapatite, carbonated hydroxyapatite, tri-calcium phosphate, carbonated hydroxyapatite, biphasic materials composed from tri-calcium phosphate and hydroxyapatite at various ratios, Si-substituted ceramics, Mg-substituted ceramics, Sr-substituted ceramics, and the like. For example, ceramic particles can include Sr-substituted ceramics, such as Sr-substituted biphasic ceramics, Sr-substituted apatite, Sr-substituted hydroxyapatite, and the like, or ceramic particles can include siliconated ceramics, such as siliconated hydroxyapatite (Actifuse Apatech) and the like. In some instances, the presence of Si ions on the surface of particles can enhance the wettability of the particles and provide enhanced interaction with polymeric compositions and blends. In some instances, ceramic particles can have a particle size of less than about 150 µm. Tables 1 and 2, discussed elsewhere herein, provide exemplary composition formulations containing ceramic components. Any wt % amounts or ranges, as well as any particle size values or ranges, mentioned with reference to Si-substituted ceramics can also apply to other ceramics such as the Sr-substituted ceramic variants disclosed herein.

Reactive Group Polymer Components

Additionally, the polymeric blends can be combined with polymers having reactive groups, such as e.g., succinimidylesters (—CON(COCH$_2$)$_2$), aldehydes (—CHO), especially succinimidylesters [—N(COCH$_2$)$_2$ as one of the component in CoSeal® (four arm PEG-NHS). In some instances, ethylene glycol polymers can be provided in a form of 4—or more arm polymers terminated with specified reactive groups. Handling properties of a bone hemostat composition may be affected by incorporating a reactive group polymer components, and in some instances the molecular weight or the concentration of the reactive group polymer component may impact such handling properties. In some cases, a PEG having a low molecular weight (and present as a liquid form) can be used to enhance or increase flexibility in a bone hemostat composition.

Oxazoline Polymer Components

Exemplary bone hemostat polymeric blends or compositions can be also formulated to include oxazoline polymers. In some instances, an oxazoline polymer can be used as a compatibilizer. In some instances, an oxazoline polymer can be used as a lubricant. In some instances, an oxazoline polymer can be used as an additive, enhancing adhesive properties of the hemostat composition, for example to enhance adhesion to bone. In some instances, an oxazoline polymer can be used as in either aqueous or nonaqueous bone hemostat compositions. In some instances, an oxazoline polymer component can be present in a bone hemostat composition within a range from about 2% to about 10% by weight of the composition.

EXAMPLES

The materials and methods of manufacture will now be further described by reference to the following non-limiting examples. Hemostatic polymeric compositions or blends can be formulated as an aqueous or non-aqueous systems.

Aqueous Systems

Examples of aqueous bone hemostat compositions are specified in Table 1.

In some instances, aqueous hemostat formulations with desirable handling properties (e.g. paste, viscous paste, or dough-like consistency) can be produced as disclosed herein. When preparing a bone hemostat containing poloxamer 407, it may be possible to achieve a viscous, moldable paste by adding about 10% by weight of water. Relatedly, it may be possible to achieve a viscous, moldable paste by adding about 5% by weight of water. In bone hemostat compositions that include crosslinked gelatin, it may be desirable to increase the amount of water and decrease the amount of poloxamer in the composition. For example, both gelatin and poloxamer may compete for water, and gelatin may swell due to its swelling capacity. In some instances, it may be possible to achieve a viscous paste (e.g. dough-like composition) by having the liquid components (e.g. water, PEG 200 Da, Pluriol V10, and the like) at about 40% to about 45% by weight of the composition, and the solid components (e.g. Poloxamer 407, crosslinked gelatin, polyoxazoline, and the like) at about 55% to about 60% by weight of the composition. According to some embodiments, the amount of crosslinked gelatin in a hemostat composition may be within a range from about 20% to about 40% by weight of the composition. In bone hemostat compositions containing chitosan or collagen, the chitosan or collagen can be similarly adjusted or selected.

In some instances, it is possible to vary the ratio between liquid components of a bone hemostat composition. For example, both PEG 200 and water have similar viscosity, and it may be possible to use less water when using more PEG 200, and conversely, it may be possible to use more water when using less PEG 200. In some cases, bone

TABLE 1

| Bone Hemostat aqueous formulation | ddH2O (wt %) | Poloxamer 407 (wt %) | Linear polyethylene oxide (PEG) (wt %) | Pluriol V10 (wt %) | Polyoxazoline (wt %) | Crosslinked gelatin particles (wt %) | Ceramic (wt %) |
|---|---|---|---|---|---|---|---|
| 1 | 44.4 | 33.3 | — | — | — | 22.2 | — |
| 2 | 24 | 26.7 | 13.3* | — | 2.7 | 33.3 | — |
| 3 | 27 | 20 | 10* | 5 | 3 | 35 | — |
| 4 | 27 | 20 | 10* | 5 | 3 | 30 | 5** |
| 5 | 27 | 20 | 10* | 5 | 3 | 30 | 5*** |

*refers to PEG with molecular weight of 200 Da
**refers to Si-substituted hydroxyapatite having a particle size below 150 μm
***refers to Sr-substituted biphasic ceramic Exemplary formulations such as those presented in Table 1 have been prepared as follows. First, specified amounts of polymers (e.g. Poloxamer 407, linear PEG, Pluriol V10, and/or polyoxazoline) were mixed with water to obtain homogenous paste. Next, gelatin particles and/or ceramic particles were added and again all components were mixed to obtain homogenous product. After mixing, the product was stable and could be applied without any further preparation onto bleeding bone. In order to preserve a moldable consistency, the aqueous systems should be protected from losing water. Examples presented in Table 1 contain crosslinked gelatin particles, but can be also formulated without gelatin. Optionally, instead of or in addition to gelatin, formulations can be prepared using chitosan and/or collagen components. Products prepared according formulations presented in Table 1 were ready-to-use bone hemostats with excellent handling properties that do not require any preparation step prior to application.

hemostat compositions may include water without including PEG 200. In some instances, random copolymer components, or polyoxazoline, may be included in a bone hemostat composition. Such ingredients may improve cohesiveness and moldability of the hemostat composition. In some cases, random copolymer components may be present in a bone hemostat composition within a range from about 2% to about 10% of the composition. In some cases, polyoxazoline may be present in a bone hemostat composition within a range from about 2% to about 10% of the composition. In some instances, ceramic particles can be included in a bone hemostat composition within a range from about 5% to about 25% by weight of the composition. In some instances, ceramic particles can be included in a bone hemostat composition within a range from about 10% to about 25% by weight of the composition. In some instances, ceramic particles can be included in a bone hemostat composition at about 5% by weight of the composition.

Nonaqueous Systems

Examples of non-aqueous bone hemostat compositions are specified in Table 2. In such systems water can still be present but at lower concentrations, for example lower than 5 wt %.

TABLE 2

| Nonaqueous Bone Hemostat formulation | Poloxamer 407 (wt %) | Pluriol V10 (wt %) | Pluronic L-31 | Pluronic L-61 | Ceramic (wt %) |
|---|---|---|---|---|---|
| 1 | 57.1 | 42.9 | — | — | — |
| 2 | 50 | 25 | 25 | — | — |
| 3 | 57.1 | 14.3 | — | 28.6 | — |
| 4 | 50 | 25 | — | 25 | — |
| 5 | 50.7 | 12.7 | — | 25.4 | 11.2* |
| 6 | 44.4 | 44.4 | — | — | 11.2** |
| 7 | 44.4 | 22.2 | 22.2 | — | 11.2** |

*refers to Si-substituted hydroxyapatite having a particle size below 150 µm
**refers to Sr-substituted biphasic ceramic Exemplary formulations such as those presented in Table 2 were prepared as follows. First, all polymeric components and selected ceramic powders were mixed at specified mass ratios at room temperature in order to obtain homogenous putty-like material. Next, this material was heated above the melting point, usually at 80° C., in order to bring all components (despite the presence of the ceramic) to a molten state. At this stage, molten material was mixed and left in an oven at 80° C. for about 30 minutes to allow air bubble to escape. Afterward, the material was removed from the oven, and cooled to room temperature or quenched in liquid nitrogen, so as to let the molten material solidify. Next, the solid material was subjected to additional mixing and homogenization process by kneading, which can also be achieved by extrusion processes such as those known in polymer technology (extrusion). After this process, the bone hemostat was ready to be packed and applied to bleeding bone without any further preparation required.

According to some embodiments, if an excessive amount of liquid components are used, a bone hemostat formulation may not perform as desired, and may be washed away by bleeding. Relatedly, if an excessive amount of solid components are used, a bone hemostat formulation may not perform as desired, and the final product may be too hard, too brittle, or not sufficiently malleable.

Exemplary products such as those prepared according the formulations presented in Table 1 provided ready-to-use bone hemostat with good handling properties that do not require any preparation step prior to application. It was also observed that exemplary products such as those prepared according to the formulations presented in Table 2 provided useful bone hemostats, and in particular, formulations 4 and 5 exhibited excellent handling properties.

Turning now to the drawings, FIG. 1 shows an aqueous bone hemostat composition according to formulation 4 of Table 1. FIG. 2 shows a non-aqueous bone hemostat composition according to formulation 2 of Table 2. FIG. 3 depicts a non-aqueous bone hemostat composition according to formulation 5 of Table 2. Hemostat compositions were also tested in a laboratory. FIG. 4 shows examples of non-aqueous bone hemostat compositions as applied to bone as part of a sternotomy procedure in heparinized pig.

Embodiments of the present invention further include methods of treating a patient or individual, which may involve administering a biocompatible composition as disclosed herein to a bone of the patient. For example, methods may include administering a bone hemostat composition to a damaged or cut bone of a patient, during a surgical procedure. Embodiments of the present invention also encompass kits for the treatment of a bone of a patient. Exemplary kits may include a bone hemostat composition as disclosed herein, and instructions for use. For example, the instructions for use may include a description of how to apply a bone hemostat composition to a bone of a patient. In some cases, the bone hemostat composition can be packaged in a container suitable for storage and/or delivery to an end user. The compositions as disclosed herein may be used in bone healing or regenerations methods and in kits for use in such methods. For example, embodiments encompass kits for repairing or treating a bone having a defect. In some cases, kits may include devices for applying or fixing the composition to the bone, such as spatulas and the like.

Where a range of values is provided, it is understood that each intervening value between the upper and lower limits of that range is also specifically disclosed, to the smallest fraction of the unit or value of the lower limit, unless the context clearly dictates otherwise. Any encompassed range between any stated value or intervening value in a stated range and any other stated or intervening value in that stated range is disclosed. The upper and lower limits of those smaller ranges may independently be included or excluded in the range, and each range where either, neither, or both limits are included in the smaller range is also disclosed and encompassed within the technology, subject to any specifically excluded limit, value, or encompassed range in the stated range. Where the stated range includes one or both of the limits, ranges excluding either or both of those included limits are also included. Value ranges may include, for example, integer ranges, numerical ranges, percentage ranges, and the like.

The subject matter of embodiments of the present invention is described herein with specificity to meet statutory requirements, but this description has been provided by way of explanation and illustration and is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Different arrangements of the components depicted in the drawings or described herein, as well as components and steps not shown or described are possible. Similarly, some features and subcombinations are useful and may be employed without reference to other features and subcombinations. Embodiments of the invention have been described for illustrative and not restrictive purposes, and alternative embodiments, and many variations in the embodiments illustrated herein, will become apparent to readers of this patent, and remain within the scope of the appended claims and their equivalents. Accordingly, the present invention is not limited to the embodiments described herein or depicted in the drawings, and various embodiments and modifications can be made without departing from the scope of the claims below.

What is claimed is:

1. A biocompatible composition for use as a bone hemostat, the composition comprising:
   an oxazoline polymer;
   water present within a range from about 20% to about 45% by weight of the composition; and a polyoxyethylene-polyoxypropylene block copolymer having a molecular weight (Mw) within a range from about 9800 Mw to about 16300 Mw.

2. A biocompatible composition according to claim 1, wherein the polyoxyethylene-polyoxypropylene block copolymer is a triblock copolymer.

3. A biocompatible composition according to claim 1, wherein the polyoxyethylene-polyoxypropylene block copolymer has a molecular weight (Mw) within a range from about 9800 Mw to about 14600 Mw.

4. A biocompatible composition according to claim 1, wherein the block copolymer comprises a percentage of polyethylene oxide within a range from about 60% to about 80%.

5. A biocompatible composition according to claim 1, wherein the block copolymer comprises a percentage of polypropylene oxide within a range from about 20% to about 40%.

6. A biocompatible composition according to claim 1, wherein the polyoxyethylene-polyoxypropylene block copolymer comprises 202 ethylene oxide units and 56 propylene oxide units.

7. A biocompatible composition according to claim 1, wherein:
the polyoxyethylene-polyoxypropylene block copolymer is present within a range from about 20% to about 80% by weight of the composition.

8. A biocompatible composition according to claim 1, further comprising a natural polymer selected from the group consisting of a gelatin, chitosan, and collagen.

9. A biocompatible composition according to claim 1, further comprising a cross linked natural polymer, wherein:
the polyoxyethylene-polyoxypropylene block copolymer is present within a range from about 20% to about 40% weight of the composition,
the cross linked natural polymer is present within a range from about 20% to about 40% weight of the composition, and
the natural polymer comprise a member selected from the group consisting of gelatin, chitosan, and collagen.

10. A biocompatible composition according to claim 1, further comprising an ethylene glycol polymer, wherein:
the oxazoline polymer is present within a range from about 2% to about 10% by weight of the composition.

11. A biocompatible composition according to claim 1, further comprising an ethylene glycol polymer and cross linked gelatin particles, wherein:
the water is present at about 24.4% by weight of the composition,
the polyoxyethylene-polyoxypropylene block copolymer is present at about 26.7% weight of the composition,
the ethylene glycol polymer is present at about 13.3% by weight of the composition,
the oxazoline polymer is present at about 2.7% by weight of the composition, and
the cross linked gelatin particles are present at about 33.3% weight of the composition.

12. A biocompatible composition according to claim 1, further comprising an ethylene glycol polymer and a random alkylene oxide copolymer.

13. A biocompatible composition according to claim 1, further comprising an ethylene glycol polymer, a random alkylene oxide copolymer, and cross linked gelatin particles, wherein:
the water is present at about 27% by weight of the composition,
the polyoxyethylene-polyoxypropylene block copolymer is present at about 20% weight of the composition,
the ethylene glycol polymer is present at about 10% by weight of the composition,
the random alkylene oxide copolymer is present at about 5% by weight of the composition,
the oxazoline polymer is present at about 3% by weight of the composition, and
the cross linked gelatin particles are present at about 35% weight of the composition.

14. A biocompatible composition according to claim 1, further comprising an ethylene glycol polymer, a random alkylene oxide copolymer and ceramic particles.

15. The biocompatible composition according to claim 14, wherein the ceramic particles comprise a member selected from the group consisting of Si-substituted ceramic particles and Sr-substituted ceramic particles.

16. The biocompatible composition according to claim 14, wherein the ceramic particles have a particle size less than about 150 µm.

17. A biocompatible composition according to claim 1, further comprising an ethylene glycol polymer, a random alkylene oxide copolymer, cross linked gelatin particles, and ceramic particles, wherein:
the water is present at about 27% by weight of the composition,
the polyoxyethylene-polyoxypropylene block copolymer is present at about 20% weight of the composition,
the ethylene glycol polymer is present at about 10% by weight of the composition,
the random alkylene oxide copolymer is present at about 5% by weight of the composition,
the oxazoline polymer is present at about 3% by weight of the composition,
the cross linked gelatin particles are present at about 30% weight of the composition, and
the ceramic particles are present at about 5% weight of the composition.

18. The biocompatible composition according to claim 17, wherein the random alkylene oxide copolymer comprises an ethylene oxide to propylene oxide ratio of about 1:1.

19. A method of treating a patient, the method comprising:
administering a biocompatible composition to a bone of the patient,
wherein the biocompatible composition comprises: an oxazoline polymer, water present within a range from about 20% to about 45% by weight of the biocompatible composition, and a polyoxyethylene-polyoxypropylene block copolymer having a molecular weight (Mw) within a range from about 9800 Mw to about 16300 Mw.

20. A method of manufacturing a biocompatible composition for use in treating a bone of a patient, the method comprising:
mixing water, a polyoxyethylene-polyoxypropylene block copolymer having a molecular weight (Mw) within a range from about 9800 Mw to about 16300 Mw, and an oxazoline polymer to form the biocompatible composition, wherein: the water is present within a range from about 20% to about 45% by weight of the biocompatible composition.

21. A biocompatible composition according to claim 17, wherein the ceramic particles comprise silicon-substituted hydroxyapatite.

22. A biocompatible composition according to claim 17, wherein the ceramic particles comprise strontium-substituted hydroxyapatite.

23. A biocompatible composition according to claim 1, further comprising a non-random copolymer component, wherein the non-random copolymer component is different from the polyoxyethylene-polyoxypropylene block copolymer.

24. A biocompatible composition according to claim 1, wherein the oxazoline polymer is a polyoxazoline.

25. A biocompatible composition according to claim 1, wherein the oxazoline polymer is present at about 3% by weight of the composition.

* * * * *